United States Patent [19]
Daley

[11] Patent Number: 6,120,526
[45] Date of Patent: Sep. 19, 2000

[54] DELIVERY DEVICES FOR BIOABSORBABLE STAPLES

[76] Inventor: Robert J. Daley, 10611 Wild Flower Rd., Orland Park, Ill. 60462

[21] Appl. No.: 09/240,042

[22] Filed: Jan. 29, 1999

[51] Int. Cl.[7] .......................... A61B 17/00; A61B 17/064
[52] U.S. Cl. ............................................. 606/219; 227/176
[58] Field of Search ..................... 606/219, 220, 606/138, 139; 227/19, 121, 129, 138, 176.1, 178, 180

[56] References Cited

U.S. PATENT DOCUMENTS

| | | |
|---|---|---|
| 3,625,220 | 12/1971 | Engelsher . |
| 3,949,924 | 4/1976 | Green . |
| 4,204,623 | 5/1980 | Green . |
| 4,489,875 | 12/1984 | Crawford et al. . |
| 4,534,350 | 8/1985 | Golden et al. . |
| 4,534,352 | 8/1985 | Korthoff . |
| 4,612,923 | 9/1986 | Kronenthal . |
| 4,635,637 | 1/1987 | Schreiber . |
| 4,646,741 | 3/1987 | Smith . |
| 4,889,119 | 12/1989 | Jamiolkowski et al. . |
| 4,950,285 | 8/1990 | Wilk . |
| 5,123,913 | 6/1992 | Wilk et al. . |
| 5,209,756 | 5/1993 | Seedhom et al. . |
| 5,258,010 | 11/1993 | Green et al. ............................ 606/219 |
| 5,282,829 | 2/1994 | Hermes . |
| 5,439,479 | 8/1995 | Shichman et al. . |
| 5,456,400 | 10/1995 | Shichman et al. . |
| 5,462,542 | 10/1995 | Alesi, Jr. . |
| 5,489,287 | 2/1996 | Green et al. . |
| 5,500,000 | 3/1996 | Feagin et al. . |
| 5,549,619 | 8/1996 | Peters et al. . |
| 5,601,604 | 2/1997 | Vincent . |
| 5,643,295 | 7/1997 | Yoon . |
| 5,693,023 | 12/1997 | Adams . |

OTHER PUBLICATIONS

Pavletic et al., Veterinary Clinics of North America: Small Animal Practice, vol. 24, No. 2, pp. 247–278, Mar. 1994.
Von Fraunhofer, Ligating Clips and Staples, in Wound Closure Biomaterials and Devices, Chu et al., Eds., pp. 307–316, CRC Press, 1997.
Steckel et al., Obstetrics & Gynecology, vol. 68, No. 3, pp. 404–410, Sep. 1986.

*Primary Examiner*—Michael Buiz
*Assistant Examiner*—(Vikki) Hoa B. Trinh
*Attorney, Agent, or Firm*—Bell, Boyd & Lloyd LLC

[57] ABSTRACT

The present invention reveals bioabsorbable staples, delivery systems for the application of the bioabsorbable staples and methods for tissue closure. The delivery systems include a semi-automatic device for applying one or more bioabsorbable staples and a manually powered device for delivering bioabsorbable staple one at a time.

7 Claims, 16 Drawing Sheets

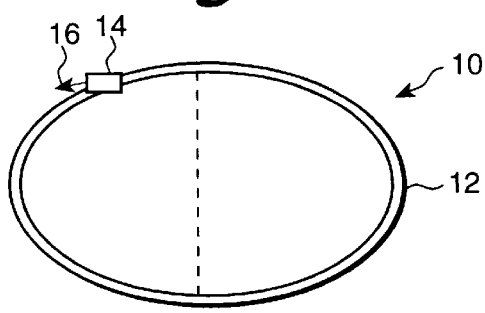
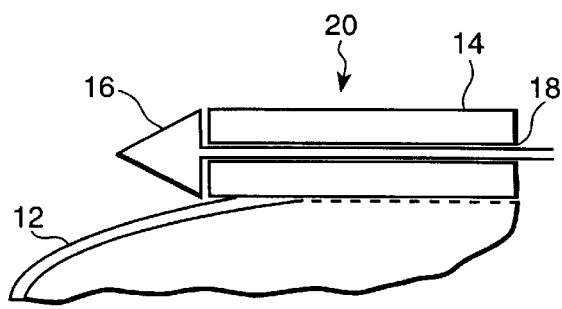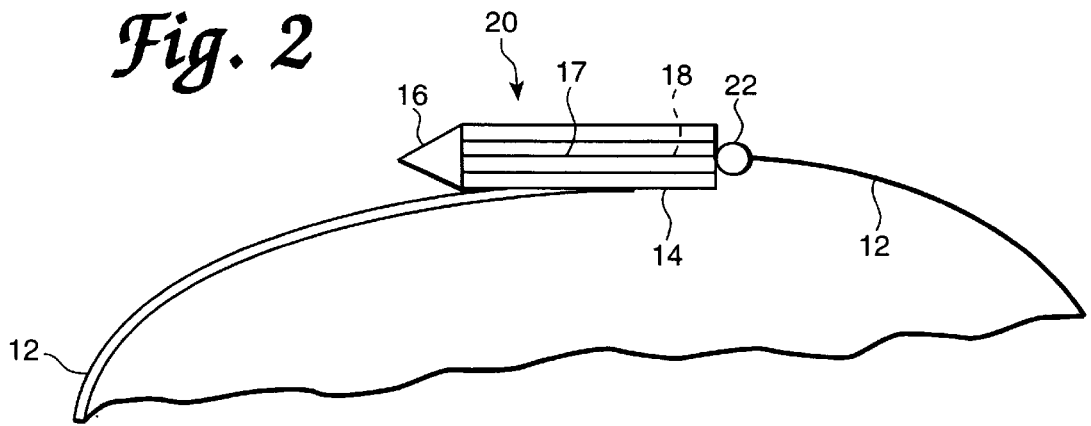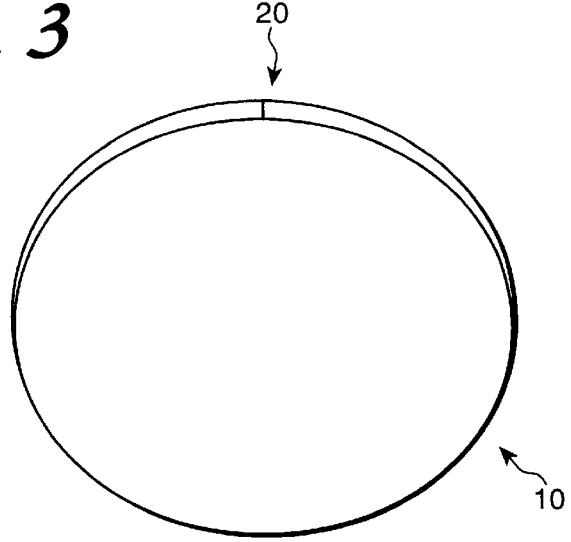

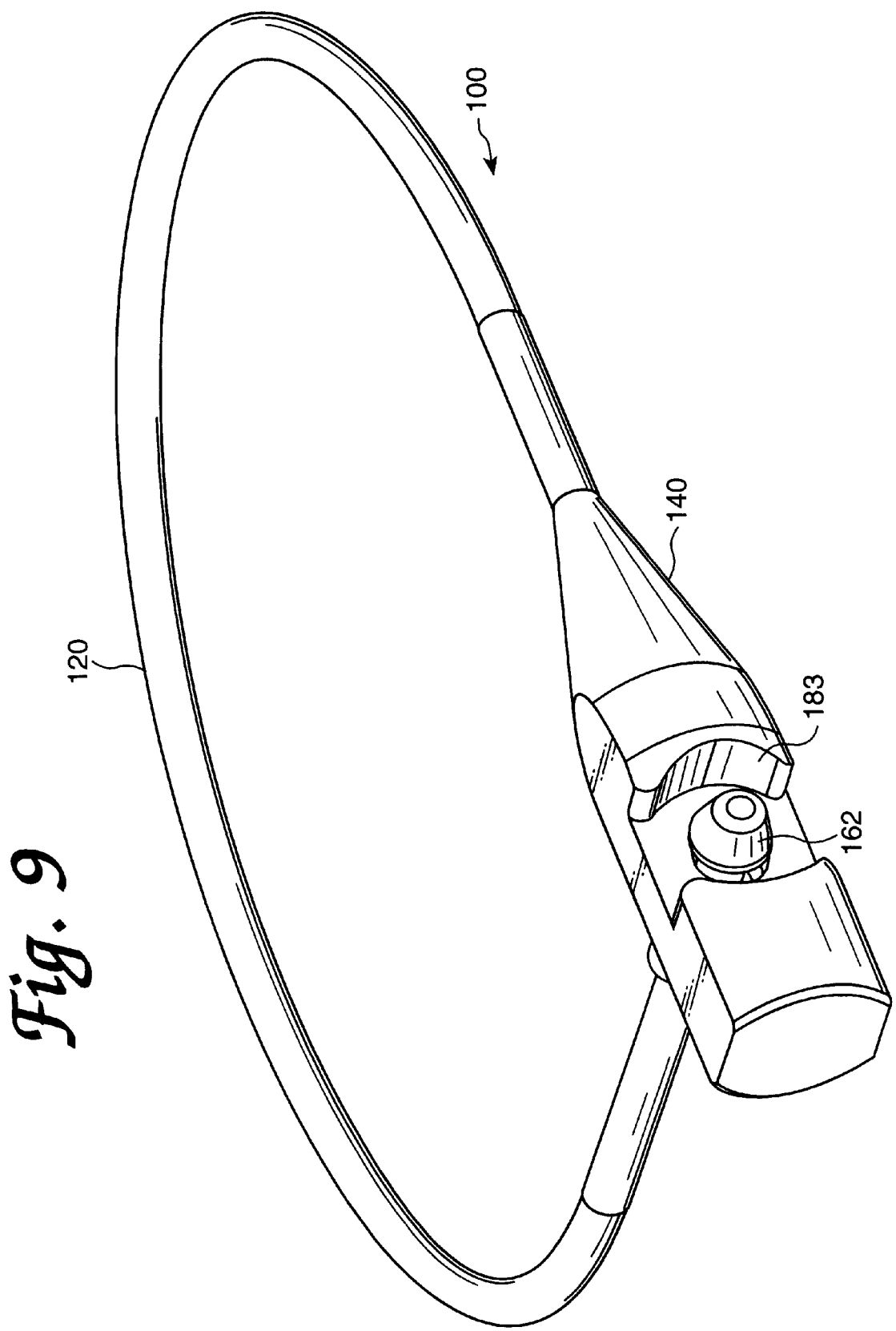

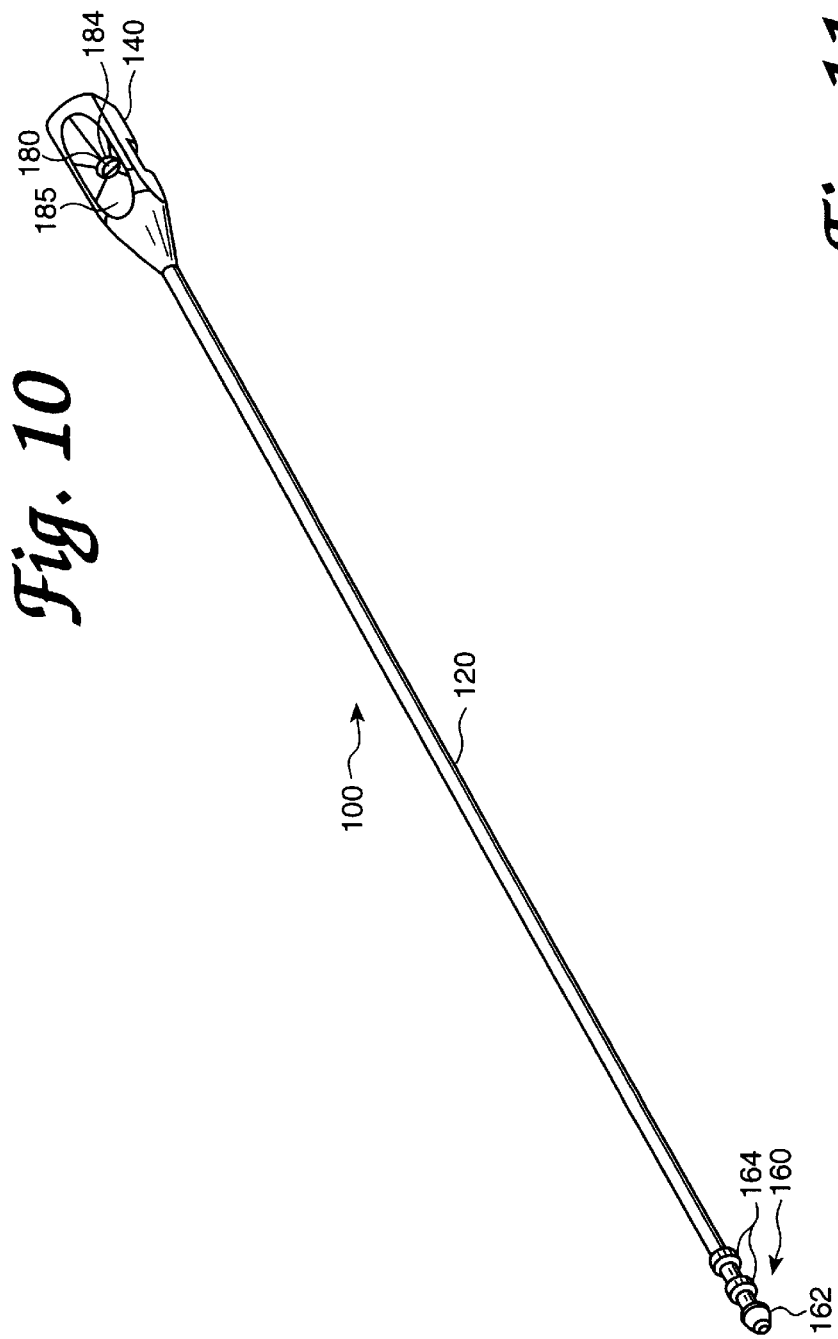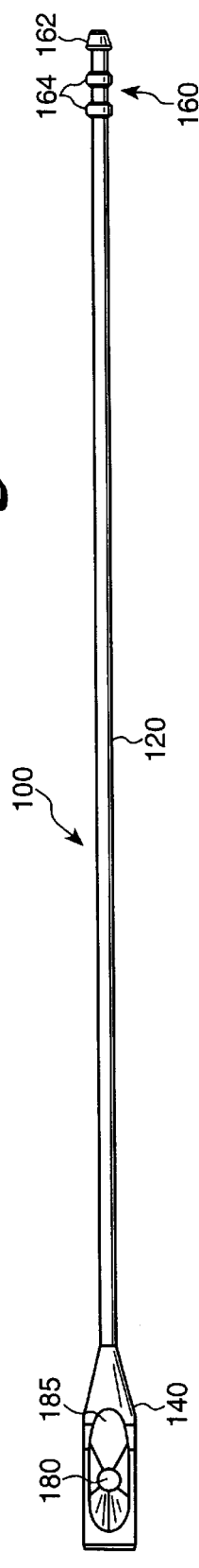

DELIVERY DEVICES FOR BIOABSORBABLE STAPLES

BACKGROUND OF THE INVENTION

1. Field of the Invention

The present invention discloses new bioabsorbable staples, new delivery systems for the application of the bioabsorbable staples and new methods for tissue closure. These bioabsorbable staples improve the consistency and reliability of the suturing process, and facilitate the wound closure process.

The first type of bioabsorbable staple is comprised of a single piece. The one-piece staple has three parts, namely, an elongated body, a retainer at one end of the elongated body, and an arrow head or connector head at the other end of the elongated body. The retainer has a tunnel passing through its core. The arrow head or connector head is inserted through the tunnel of the retainer and forms a secure lock with the retainer. The secured arrow head or connector head, retainer and elongated body form a closed ellipsoid suture structure.

The other type of bioabsorbable staple is comprised of two pieces. The two-piece staple or suture is comprised of a first elongated body having a leg connected to an arrow head at each end and a second elongated body having a retainer at each end, where each retainer contains an eyelet. The arrow heads are separately inserted into the eyelets of the retainers. The secured arrow heads, retainers and elongated bodies form a closed ellipsoid suture structure.

The staples are delivered through a separate staple delivery device. The first type of delivery device is a manually powered instrument for applying one bioabsorbable staple at a time. The second type of delivery device is semi-automatic for applying one or more bioabsorbable staples.

2. Description of the Related Art

Because of the advantages over conventional suturing techniques, mechanical stapling is now widely used in surgical procedures. Wound closure with stainless steel staples has resulted, for example, in decreased tissue trauma, a reduction in the length of hospital stay, and a lower infection rate (see, for example, Steckel et al., Experimental Evaluation of Absorbable Copolymer Staples for Hysterectomy, *Obstetrics & Gynecology,* Vol. 68, No. 3, pp. 404–410, September 1986).

Numerous types of surgical staples have been reported. For example, U.S. Pat. No. 3,625,220 (Engelsher) discloses a suture guard device comprised of an outer tube, an inner tube, and a locking means. The suture guard is semirigid and preferably made of polyethylene.

U.S. Pat. No. 4,534,350 (Golden et al.) discloses a two-piece tissue fastener comprised of an open loop fastening member having two legs with rows of rounded protrusions and a receiver. The legs of the fastening member are inserted into bores of the receiver and the rounded protrusions cooperate with a bore to form a secure connection.

Both U.S. Pat. No. 4,950,285 (Wilk) and U.S. Pat. No. 5,123,913 (Wilk et al.) disclose a one-piece suture device comprised of:

a) a thread provided with a series of resilient projections along a portion of its length, b) a loop defining an opening, c) a joining means for connecting one end of the thread to the loop, and d) locking means.

U.S. Pat. No. 5,601,604 (Vincent) discloses a one-piece gastric band comprised of a body portion with a tail end and a buckle. The tail end of the body portion is inserted into the buckle to form a loop.

However, none of these patents disclose bioabsorbable staples and all are patentably distinguishable over the bioabsorbable staples of the present invention. Furthermore, none of these patents is believed to have any direct relevance to the patentability of the bioabsorbable staples of the present invention.

Although the advantages of stapling are numerous, complications associated with the use of steel staples led to the development of bioabsorbable staples.

Bioabsorbable staples were developed by combining different concentrations of lactide and glycolide, polymerized under varying conditions to enhance their rate of hydrolysis and absorption from tissues. In the early 1980s, lactomer absorbable plastic staples, e.g., polysorb, became available for use in hysterectomy in women. Lactomer staples are hard and opaque, and are unlike conventional metallic staples in that they are not bent during their application to form the shape of a "B". Rather, each copolymer staple is composed of two parts: a "U"-shaped fastener and an "8"-shaped retainer. When the stapling instrument is fired, the fastener is forced through the tissue and locks into its retainer. Currently available lactomer staples retain about 75% of their initial strength during the first postoperative week, with 40% tensile strength retention at about 2 weeks. The staples begin fragmenting after 3 to 4 weeks, and absorption follows.

Numerous types of bioabsorbable surgical staples have been reported. For example, U.S. Pat. No. 4,534,352 (Korthoff) discloses a two-piece surgical fastener made from an absorbable resinous material. The surgical fastener is comprised of a base and a prong-containing member. Each prong is inserted into an aperture in the base to form a secure connection.

U.S. Pat. No. 4,612,923 (Kronenthal) discloses a two-piece surgical fastener made from a synthetic absorbable polymer containing an absorbable glass filler. The surgical fastener is comprised of a staple and a receiver. The staple is inserted into openings in the receiver to form a secure connection.

U.S. Pat. No. 4,646,741 (Smith) discloses a two-piece surgical staple made from a blend of a lactide/glycolide copolymer and poly(p-dioxanone). The surgical staple is comprised of a base with two legs and a receiver. The legs of the base are inserted into receptacles in the receiver to form a secure connection.

U.S. Pat. No. 4,889,119 (Jamiolkowski et al.) discloses a two-piece surgical fastener made from a glycolide-rich blend of two or more polymers. The surgical fastener is comprised of a base with two legs and a receiver. The legs of the base are inserted into receptacles in the receiver to form a secure connection.

U.S. Pat. No. 5,282,829 (Hermes) discloses a two-piece biodegradable surgical device comprised of a fastener with two prongs and a receiver. The prongs of the fastener are inserted into the receiver to form a secure connection. Both the fastener and the receiver contain a hollow core region.

U.S. Pat. No. 5,439,479 (Shichman et al.) discloses a biodegradable two-piece surgical clip comprised of a fastener and a retainer. The fastener has a set of legs containing gripping means adapted to be engaged by the retainer. When the legs of the fastener are engaged by the retainer, a closed connection is formed.

U.S. Pat. No. 5,462,542 (Alesi, Jr.) discloses a biodegradable one-piece surgical strap assembly having a flexible elongated strap and a buckle attached to one end of the strap. A portion of the strap contains a plurality of ratchet teeth. The ratchet teeth of the strap engage a locking mechanism in the buckle to form a loop.

U.S. Pat. No. 5,549,619 (Peters et al.) discloses a biodegradable one-piece or two-piece surgical device comprised of an eye with a latching pawl and a flexible strip with ratchet teeth. The ratchet teeth of the flexible strip engage with the latching pawl of the eye to form a loop.

U.S. Pat. No. 5,643,295 (Yoon) discloses an apparatus for suturing tissue comprised of a knotting element connected between two length portions of filamentous suture material to form a contractile loop for confining segments of the length portions therein.

However, each of these patents is patentably distinguishable over the bioabsorbable staples of the present invention and none of these patents is believed to have any direct relevance to the patentability of the bioabsorbable staples of the present invention.

Likewise, numerous types of surgical staple delivery systems have been reported. For example, U.S. Pat. No. 3,949,924 (Green) discloses a manually powered surgical stapling instrument for stapling together skin or fascia. The instrument has a main body with a nose portion that has means for advancing and forming staples around an anvil.

U.S. Pat. No. 4,204,623 (Green) discloses a manually powered surgical stapling instrument for applying sterilized staples to disunited skin or fascia. A pusher is slidably mounted in the cartridge for advancing the stales, for ejecting the staples and for forming the staples around an anvil.

U.S. Pat. No. 4,489,875 (Crawford et al.) discloses an instrument for applying staples to skin by bending the staple around an anvil. As the staple is forced against the anvil, the staple bends and the legs penetrate the tissue and apply closing pressure across the wound.

However, each of these patents is patentably distinguishable over the bioabsorbable staple delivery systems of the present invention and none of these patents is believed to have any direct relevance to the patentability of the delivery systems of the present invention.

A thorough review of the field of bioabsorbable staples and stapling instrumentation has been reported by Michael M. Pavletic and Anthony Schwartz in *Veterinary Clinics of North America: Small Animal Practice,* Volume 24, Number 2, pages 247–278, March 1994, and by Chih-Chang Chu, Anthony von Fraunhofer and Howard Greisler, "Wound Closure Biomaterials and Devices", CRC Press, Inc., 1997.

SUMMARY OF THE INVENTION

The present invention discloses bioabsorbable staples, delivery systems for the application of the bioabsorbable staples and methods for tissue closure. The first type of staple is a one-piece staple for tissue closure, comprising:

a) an elongate body, and b) a locking mechanism, where the locking mechanism comprises i) a retainer having an enclosed central tunnel and is located or situated at the first end of the elongate body, and ii) an arrow head located or situated at the second end of the elongate body, where the staple is bioabsorbable and forms an ellipsoid structure when the arrow head is inserted into the tunnel of the retainer of the locking mechanism.

In another embodiment of the one-piece staple, the locking mechanism further comprises a locking bead situated on the elongate body behind the arrow head at the second end of the elongate body. When the arrow head is inserted into the tunnel of the retainer of the locking mechanism, the arrow head contacts the first end of the retainer and the locking bead contacts the second end of the retainer.

In another embodiment of the one-piece staple, the locking mechanism further comprises a retainer having an interior ledge at one end of the tunnel. When the arrow head is inserted into the tunnel of the retainer of the locking mechanism, the arrow head engages the interior ledge of the tunnel. In another aspects of this embodiment, the tunnel has a single opening and the interior ledge is located at the end of the tunnel having the opening.

In a most preferred embodiment of the one-piece staple, the ellipsoid structure formed when the arrow head is inserted into the retainer of the locking mechanism has a smooth, tapered, and continuous outer surface, as seen in FIG. 3.

In each of the above-given embodiments, the arrow head may be solid or may be comprised of a hollow outer cone and a shaft which is continuous with the elongate body. In the later embodiment, the hollow cone collapses when passing through the tunnel of the retainer and returns to its original shape when the arrow head is completely inserted through the tunnel of the retainer of the locking mechanism.

In another preferred embodiment, the one-piece bioabsorbable staple for tissue closure is comprised of:

a) an elongate body having a long axis, and b) a locking mechanism, where the locking mechanism comprises i) a retainer having an enclosed central tunnel, the retainer located at a first end of the elongate body, the enclosed central tunnel having a first open end and a second open end and the enclosed central tunnel aligned perpendicular to the long axis of the elongate body, and ii) an arrow head or connector head located at a second end of the elongate body, wherein the arrow head or connector head comprises an insertion piece at the second end of the elongate body and at least one locking piece, wherein the staple is bioabsorbable and forms an ellipsoid structure when the arrow head or connector head is inserted into the tunnel of the retainer of the locking mechanism.

In a more preferred embodiment of this bioabsorbable staple, the insertion piece of the arrow head or connector head is situated at the first open end of the enclosed central tunnel and the at least one locking piece is situated at the second open end of the enclosed central tunnel when the bioabsorbable staple is in a locked position.

In a most preferred embodiment of this bioabsorbable staple, the retainer further comprises a recess surrounding the second open end of the enclosed central tunnel and a recess partially surrounding the first open end of the enclosed central tunnel.

The one-piece bioabsorbable staples may be constructed from polydiaxanone, a copolymer of glycolic acid and lactic acid, or a blend of polydiaxanone and a copolymer of glycolic acid and lactic acid. Polydiaxanone is particularly preferred for the construction of the one-piece staple.

The method for tissue closure with the one-piece staple comprises the steps of grasping and holding the tissue to be closed, forcing a one-piece bioabsorbable staple through the tissue, and locking the staple.

In a most preferred embodiment of the method, the one-piece bioabsorbable staple has a smooth, tapered, and continuous outer surface, as seen in FIG. 3.

The one-piece bioabsorbable staples used in the method may be constructed from polydiaxanone, a copolymer of glycolic acid and lactic acid, or a blend of polydiaxanone and a copolymer of glycolic acid and lactic acid. Polydiaxanone is particularly preferred in the method.

The second type of staple is a two-piece staple for tissue closure, comprising:

a) a first elongate body having a leg connected to an arrow head at each end; and b) a second elongate body having a retainer at each end, where each retainer contains an eyelet. In this type of staple, each arrow head of the first elongate body engages with an eyelet of the retainer of the second elongate body. Furthermore, the staple is bioabsorbable and forms an ellipsoid structure when the arrow heads of the first elongate body engage with the eyelets of the retainer of the second elongate body.

With this type of staple, the arrow head is preferably solid and may be constructed from polydiaxanone, a copolymer of glycolic acid and lactic acid, or a blend of polydiaxanone and a copolymer of glycolic acid and lactic acid. A copolymer of glycolic acid and lactic acid is particularly preferred for the construction of the two-piece staple.

The method for tissue closure with the two-piece staple comprises the steps of grasping and holding the tissue to be closed, forcing a two-piece bioabsorbable staple through the tissue, and locking the staple.

For the one-piece staple, the two-piece staple, and the respective methods for tissue closure, the tissue can be selected from the group consisting of fascia, tendon, muscle, and ligament.

A device for applying one or more staples to tissue is comprised of a main body portion having a nose portion connected to a handle portion and a handle trigger reciprocately connected to the handle portion of the main body portion. The nose portion comprises a main channel, a swivel channel, a rod in contact with the swivel channel and a plunger in contact with the main channel and the rod. The handle portion comprises a link in contact with the plunger. Activation of the handle trigger causes advancement of the link which advances the plunger which causes the rod to advance and swing the swivel channel into contact with the main channel and advancement of a staple through the main channel and the swivel channel.

The device may further comprise a cam and spring in contact with the plunger; an inner lower head housing for attachment of the main channel and the swivel channel; and an upper head housing in contact with an outer lower head housing, where the upper head housing and the outer lower head housing surround the nose portion of the main body portion.

A method for closure of a tissue with the device comprises grasping and holding a tissue to be closed; forcing a bioabsorbable staple through the tissue with the device; and locking the staple. In a preferred embodiment of the method, the forcing step further comprises pushing an end of the main channel through a first side of the tissue to be closed, pulling a second side of the tissue into contact with the first side of the tissue, pushing an end of the swivel channel through the second side of the tissue and into contact with the end of the main channel, and advancing a staple through the main channel and the swivel channel.

BRIEF DESCRIPTION OF THE DRAWINGS

FIG. 1A shows one embodiment of the one-piece bioabsorbable staple of the present invention.

FIG. 1B shows a close up of the retainer and the arrow head of the one-piece bioabsorbable staple of FIG. 1A.

FIG. 2 shows a close up of another embodiment of the arrow head of the one-piece bioabsorbable staple of FIG. 1A.

FIG. 3 shows another embodiment of the one-piece bioabsorbable staple of the present invention.

FIG. 9 shows a reverse angle view of the preferred embodiment of FIG. 8.

FIG. 10 shows an top view of the preferred embodiment of FIG. 8 in an elongated or unlocked state.

FIG. 11 shows an side view of the preferred embodiment of FIG. 8 in an elongated state.

DETAILED DESCRIPTION OF THE PREFERRED EMBODIMENT

Figure 4:
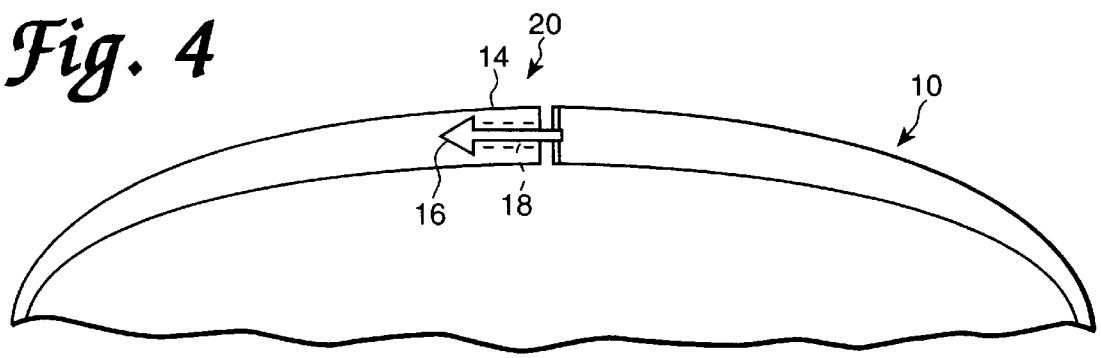
FIG. 4 shows a close up of the retainer and the arrow head of the one-piece bioabsorbable staple of FIG. 3.

The present invention discloses new bioabsorbable staples, new delivery systems for the application of the bioabsorbable staples and methods for tissue closure. The tissue can be selected from the group consisting of fascia, tendon, muscle, and ligament. The present invention is exceptionally suited for fascia closure.

The bioabsorbable staples may be made of any bioabsorbable material such as, for example, polydiaxanone or polysorb, a copolymerized glycolic and lactic acid, or a blend of polydiaxanone and a copolymer of glycolic and lactic acid. The polysorb is also known as lactomer. The staples are used for tissue closure, improve the consistency and reliability of the suturing process, and facilitate the wound closure process. The staples are delivered through a separate staple delivery device, described below.

The first type of bioabsorbable staple is comprised of a single piece. The one-piece staple 10, as seen in FIG. 1A, has three parts, namely, an elongate body 12, a retainer 14 at one end of the elongate body 12, and an arrow head 16 at the other end of the elongate body 12. The retainer 14 has a central tunnel 18 passing through its core, as seen in FIG. 1B. The arrow head 16 is attached to a shaft 17, best seen in FIGS. 2, 7A, and 7B, which is continuous with the elongate body 12. The arrow head 16 is inserted through the tunnel 18 of the retainer 14 and forms a secure lock or locking mechanism 20 with the retainer 14. The secured arrow head 16, retainer 14, and elongate body 12 form a closed ellipsoid staple structure 10. The staples are delivered through a separate staple delivery device, described in detail below.

Figure 6A:
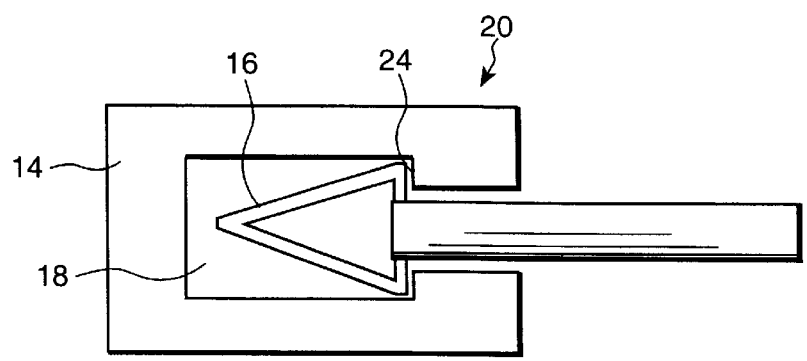
FIGS. 6A and 6B show other embodiments of the locking mechanisms of the present invention.
Figure 6B:
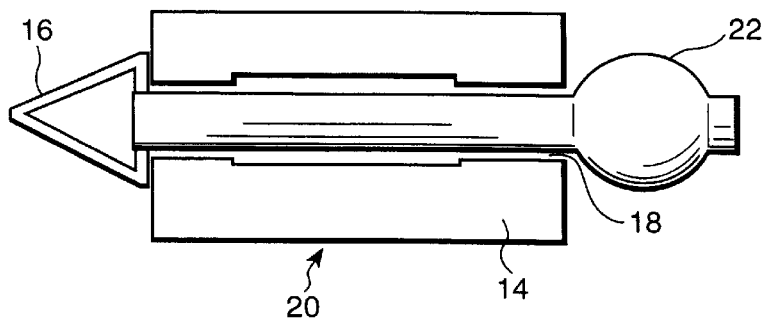

The locking mechanism 20 can be further constructed to contain a locking bead 22 situated behind the arrow head 16 at the second end of the elongate body 12, as seen in FIGS. 2 and 6B. In this embodiment, the arrow head 16 contacts the first end of the retainer 14 and the locking bead 22 contacts the second end of the retainer 14 when the arrow head 16 is inserted into the tunnel 18 of the retainer 14 of the locking mechanism 20.

The locking mechanism 20 can be further constructed to contain a retainer 14 having an interior ledge 24 at one end of the tunnel 18. In this embodiment, seen in FIG. 6A, the arrow head 16 engages the interior ledge 24 of the tunnel 18 when the arrow head 16 is inserted into the tunnel 18 of the retainer 14 of the locking mechanism 20.

In another embodiment, the ellipsoid structure 10 formed when the arrow head 16 is inserted into the retainer 14 of the locking mechanism 20 has a smooth, tapered, and continuous outer surface, as seen in FIG. 3. This same configuration is seen in cross-section in FIG. 4.

More specifically, the locking mechanism 20 is contained within the body of the staple 10 so that the arrow head 16 is buried inside the tunnel 18 of the retainer 14 of the locking mechanism 20. This configuration results in a staple 10 having a smooth, tapered, and continuous outer surface.

Figure 7A:
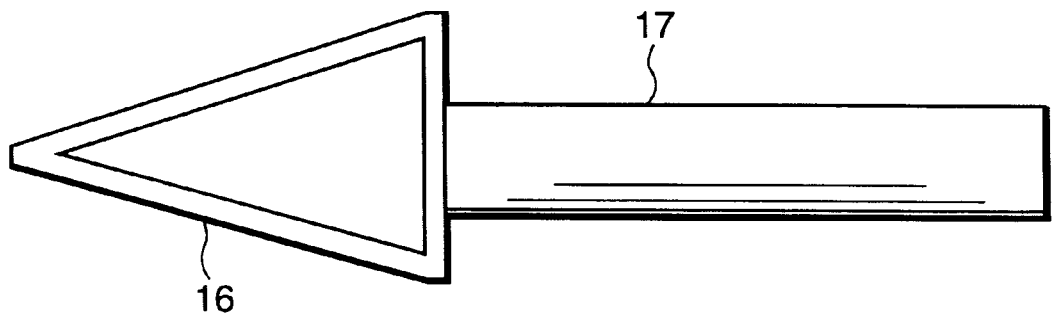
FIGS. 7A and 7B show embodiments of the retainer and arrow head of the present invention.
Figure 7B:
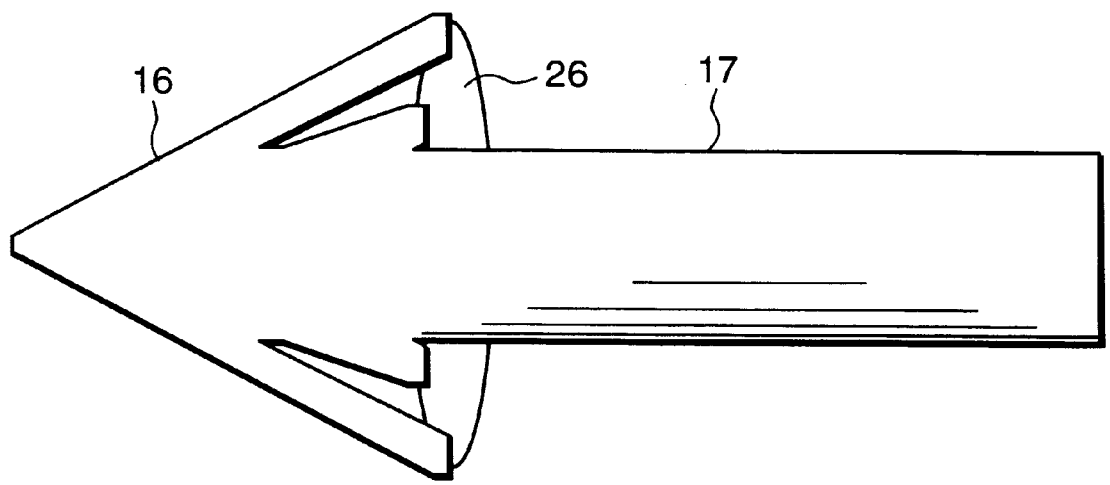
Figure 8:
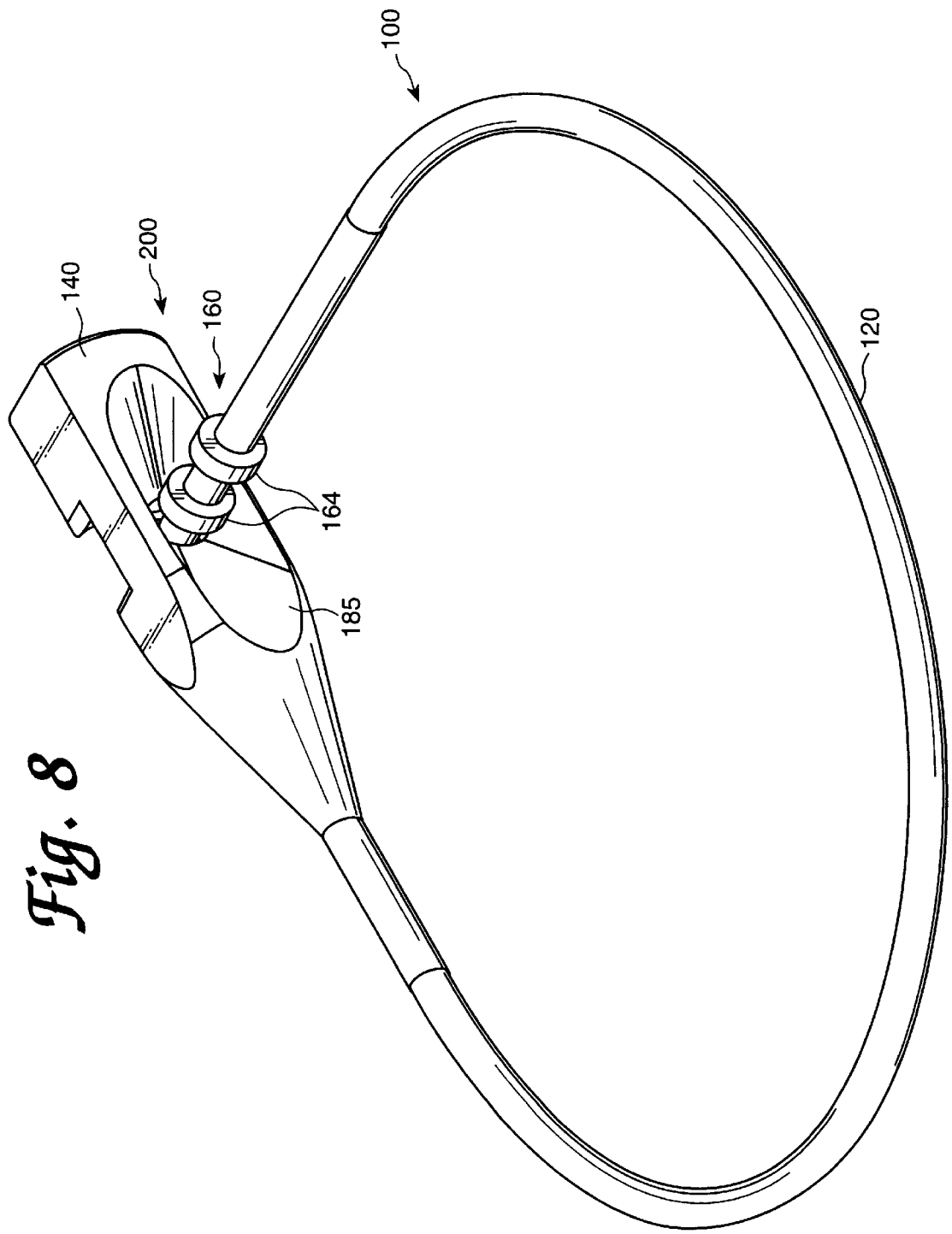
FIG. 8 shows a preferred embodiment of a one-piece bioabsorbable staple of the present invention in a locked position.
Figure 12:
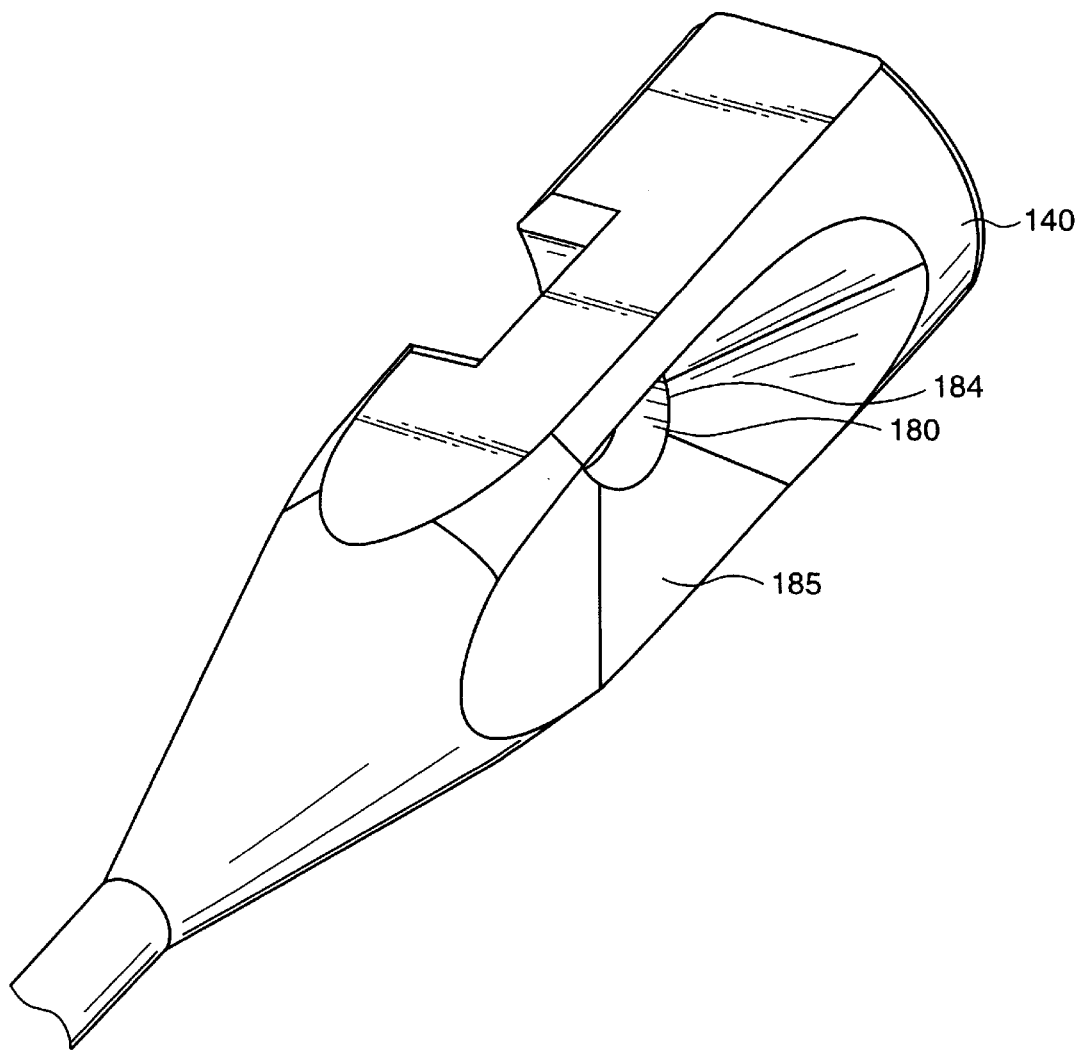
FIG. 12 is a close up of the retainer of the preferred embodiment of FIG. 8.
Figure 13:
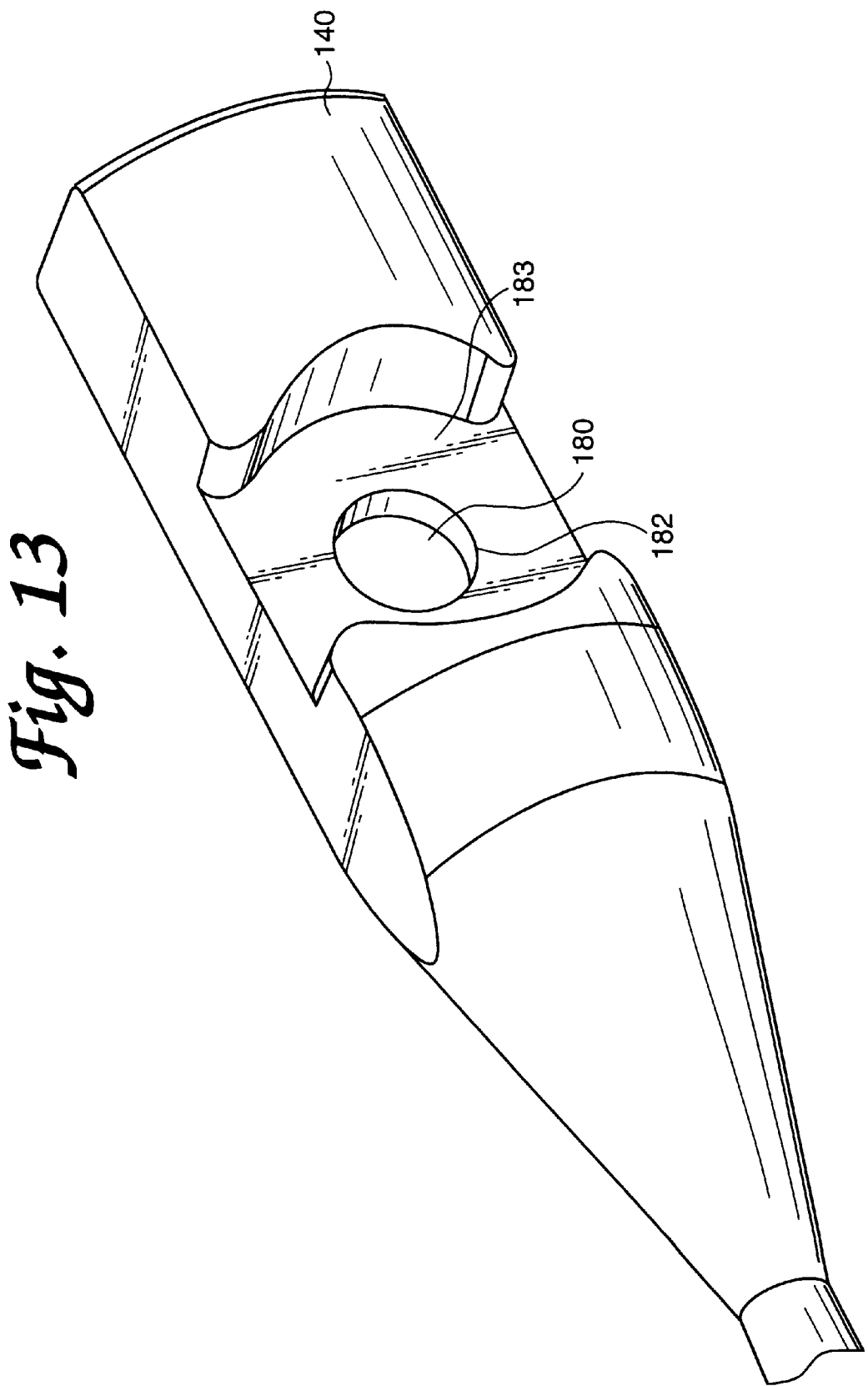
FIG. 13 is a reverse angle of the close up of the retainer of the preferred embodiment of FIG. 8.
Figure 14:
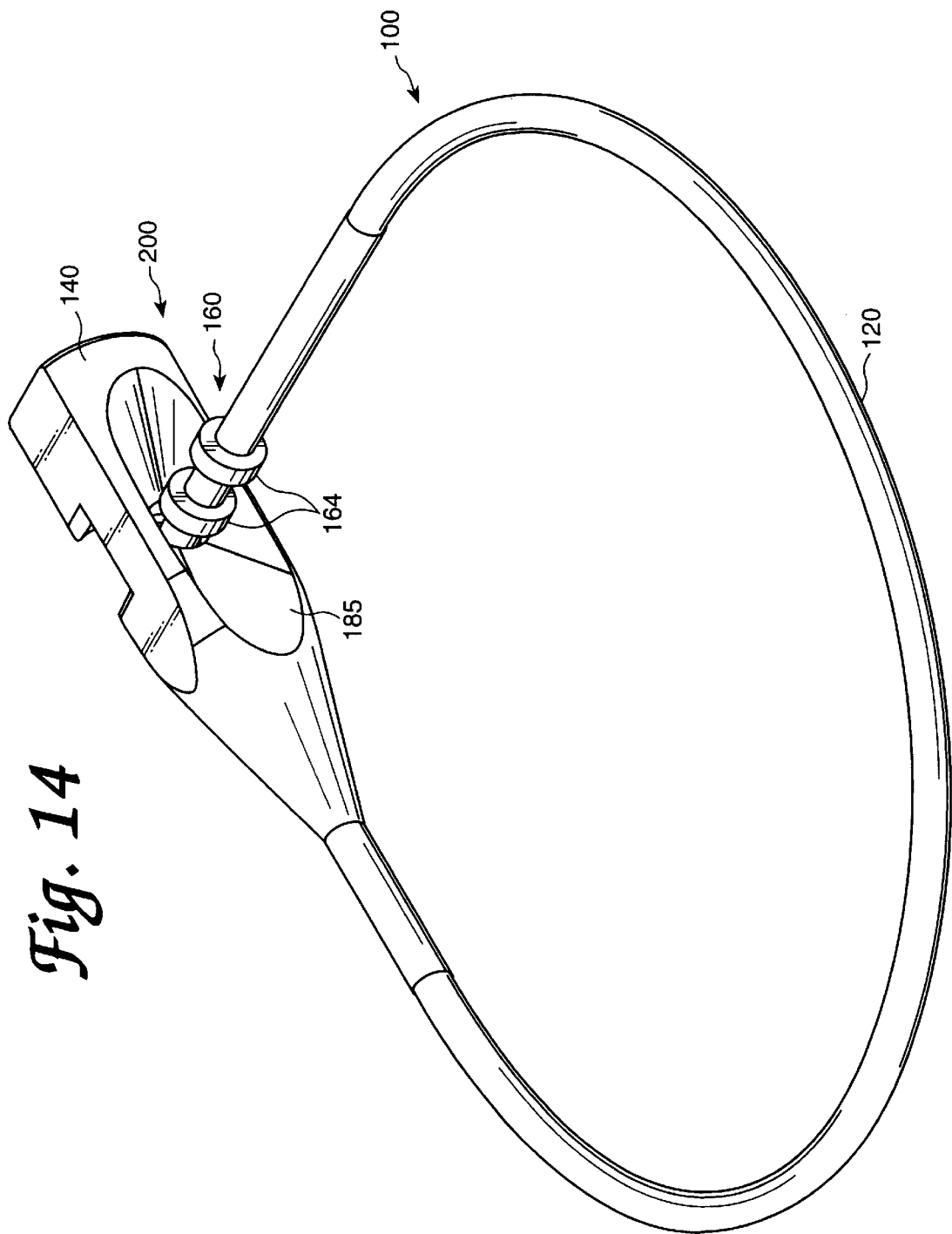
FIG. 14 shows a diagrammatic representation of the preferred embodiment of a one-piece bioabsorbable staple of FIG. 8.
Figure 15:
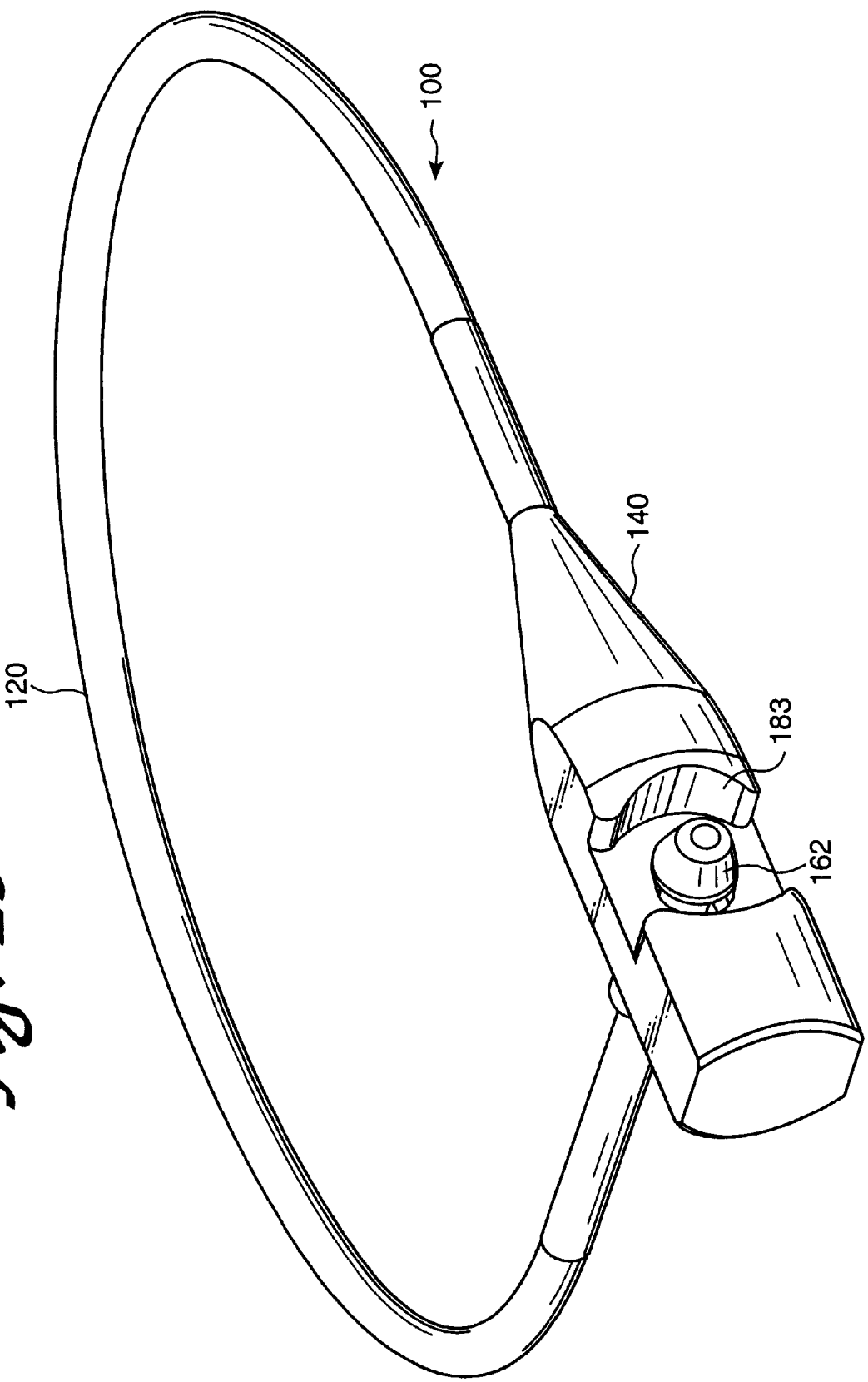
FIG. 15 shows a reverse angle view of the diagrammatic representation of the preferred embodiment of FIGS. 8 and 14.

The arrow head 16 may be solid as seen in FIG. 7A. The arrow head 16 may also be constructed of a hollow outer cone 26 and an inner shaft 17 which is continuous with the elongate body 12. In this embodiment, the cone 26 collapses when passing through the tunnel 18 of the retainer 14 and returns to its original shape when the arrow head 16 is completely inserted through the tunnel 18 of the retainer 14 of the locking mechanism 20.

FIGS. 8–16 disclose a preferred embodiment of the one-piece staple for tissue closure. The one-piece staple 100, as seen in FIGS. 8–11 and 14–15, has three parts, namely, an elongate body 120 having a long axis, a retainer 140 at a first end of the elongate body 120, and an arrow head or connector head 160 at a second end of the elongate body 120.

The retainer 140 has an enclosed central tunnel 180 passing through its core, as best seen in FIGS. 10–13. The central tunnel 180 has a first open end 182 and a second open end 184. The enclosed central tunnel 180 is aligned perpendicular to the long axis of the elongate body 120 (see FIGS. 8–11 and 14–15). The retainer 140 has a recess around each open end of the central tunnel 180. A first recess 183 partially surrounds the first open end 182 of the enclosed central tunnel 180 and protects the insertion piece 162 from physical contact when the bioabsorbable staple is in a locked position. A second recess 185 surrounds the second open end 184 and facilitates entry of the insertion piece 162 into the second open end 184 of the central tunnel 180 when the bioabsorbable staple is being placed into a locked position.

The connector head 160 is continuous with the elongate body 120 and is located at the second end of the elongate body 120. The connector head is comprised of the insertion piece 162 at the second end of the elongate body followed by at least one locking piece 164.

In the locking process, the insertion piece 162 of the connector head 160 is inserted through the second open end 184 and then through the first open end 182 of the enclosed central tunnel 180 of the retainer 140. In this manner, the insertion piece 162 of the connector head 160 becomes situated at the first open end 182 of the enclosed central tunnel 180 and the locking piece 164 becomes situated at the second open end 184 of the enclosed central tunnel 180 when the bioabsorbable staple is in the locked position. In other words, the connector head 160 is inserted through the second open end 184 of the enclosed central tunnel 180 of the retainer 140 and forms a secure lock or locking mechanism 200 with the retainer 140.

Figure 16:
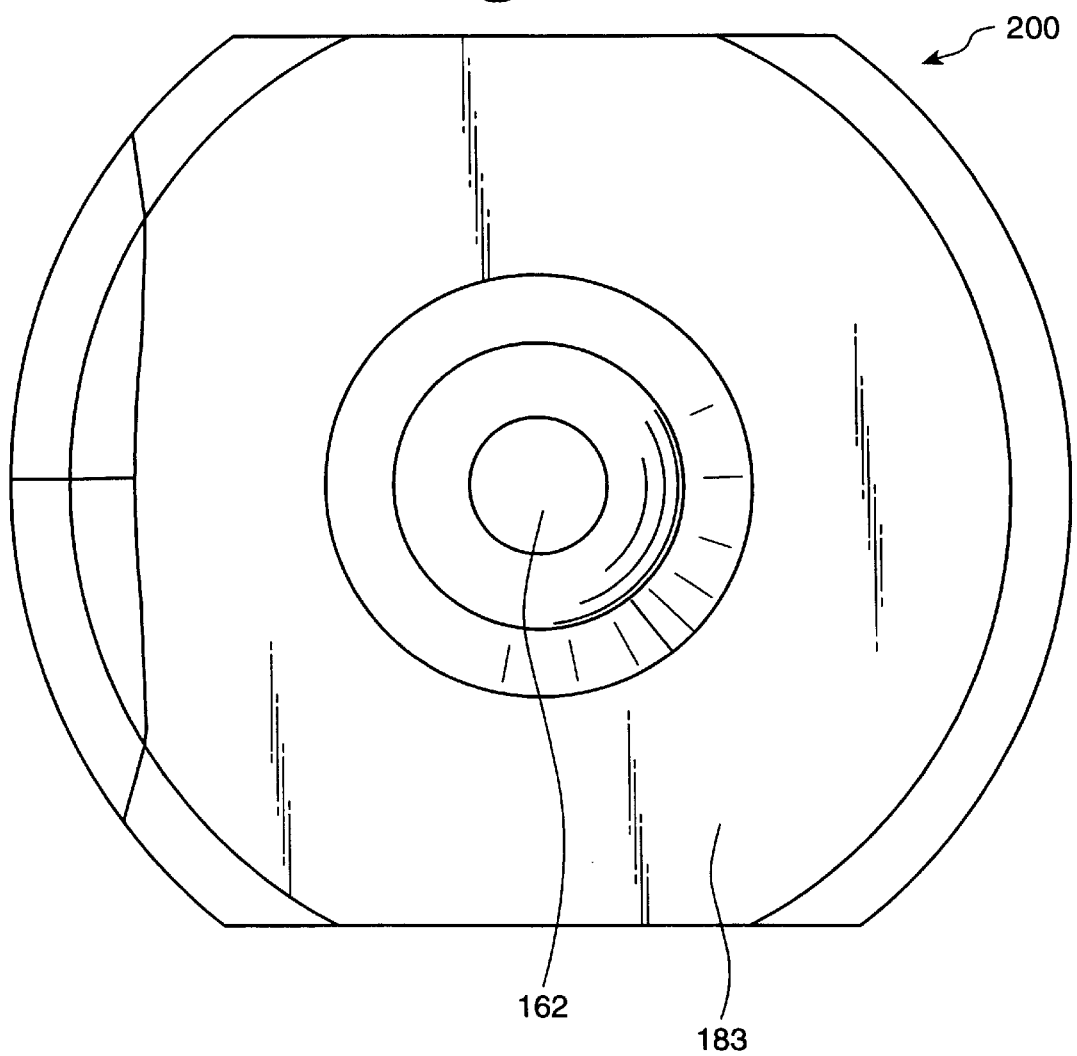
FIG. 16 is a diagrammatic representation of a frontal view of the locking mechanism of the preferred embodiment of FIG. 8.

FIG. 16 is a diagrammatic representation of a frontal view of the locking mechanism 200, showing the first recess 183 and the insertion piece 162. The secured connector 160, retainer 140, and elongate body 120 form a closed ellipsoid staple structure 100 in the locked position (FIGS. 8–9 and 14–15). The staples are delivered through a separate staple delivery device.

Figure 5:
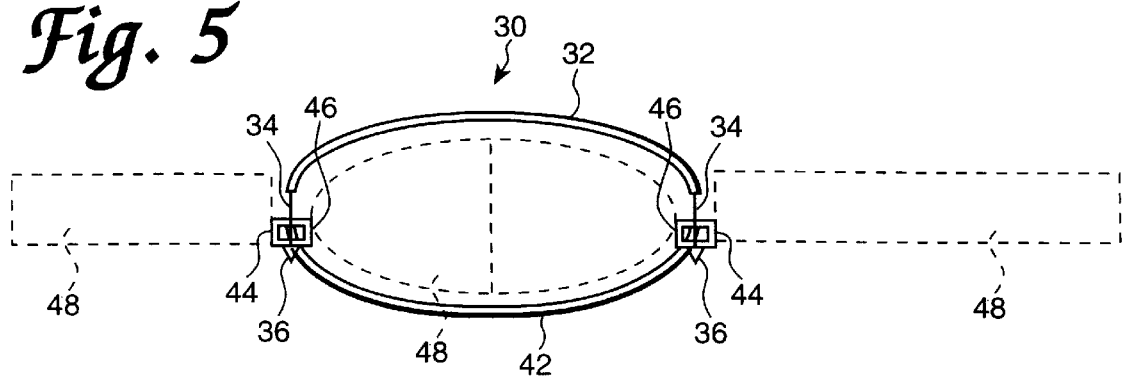
FIG. 5 shows one embodiment of the two-piece bioabsorbable staple of the present invention.

The second type of bioabsorbable staple is comprised of two pieces. The staple 30, seen in FIG. 5, has two parts. A first elongate body 32 has a leg 34 connected to an arrow head 36 at each end. The second elongate body 42 has a retainer 44 at each end. Each retainer 44 contains an eyelet 46, where each arrow head 36 of the first elongate body 32 engages with an eyelet 46 of the retainer 44 of the second elongate body 42. When the arrow heads 36 of the first elongate body 32 engage with the eyelets 46 of the retainer 44 of the second elongate body 42, an ellipsoid structure 30 is formed around the tissue 48 being closed.

In other words, the arrow heads 36 are separately inserted into the eyelets 46 of the retainers 44. Thus, the first arrow head 36 of the first elongate body 32 is inserted into the eyelet 46 of the first retainer 44 of the second elongate body 42. The second arrow head 36 of the first elongate body 32 is inserted into the eyelet 46 of the second retainer 44 of the second elongate body 42. The secured arrow heads 36, retainers 44, and elongate bodies 32 and 42 form a closed ellipsoid suture structure 30.

The first type of staple delivery device is a manually powered instrument for appyling the bioabsorbable staples of the present invention to fascia, muscle, tendon or skin. The surgical instrument is made of two elongated bodies. The first elongated body has a first end, a handle at the first end and a second end. The second elongated body has a first end, a handle at the first end and a second end. The second end of the second elongated body forms a circular formation. The elongated bodies are pivotally connected at a distance from the first end, respectively, of each body.

The device holds one staple in the mouth of the instrument (the opening between the two staple arms). The staple is held in a groove in each arm in the open position. The soft tissue is brought into the opening of the mouth of the device. The handles are then brought together which close the staple arms together. This brings the staple through the soft tissue and locks the staple together. The handles are then allowed to open, which opens the staple arm. This releases the locked staple around the tissue from the device.

A second type of staple delivery device is a semi-automatic instrument, as seen in FIGS. 17–21. The instrument is tension loaded and the delivery end of the instrument and handle resemble a pistol with a swivel barrel option. The device forces the staple through the tissue and locks it into a retainer. Soft tissue tensioning is controlled by how much soft tissue is place within the device. There is a plurality of staples within the device. After the staple is inserted it has an ellipsoid or curvilinear structure with convexity out for maximum purchase of soft tissue.

The device has a housing that represents the main body portion. It has a handle trigger for actuating the device. The nose portion has the means for applying the staples. Located in the housing is a plurality of staples in an array acting to mount a plunger for advancing and locking an individual staple.

More specifically, the device 300 is comprised of the following components:

right handle housing 302;
left handle housing 304;
handle trigger 306;
link 308;
cam 310;
upper head housing 312;
inner lower head housing 314;
outer lower head housing 316;
main channel 318;
swivel channel 320;
plunger 322;
rod 324; and
track 326.

The handle trigger 306 is positioned between the right handle housing 302 and the left handle housing 304. The housing links the handle mechanism to the plunger mechanism. The handle trigger 306 transmits the gripping and squeezing force from the hand of the user to transform that force into the force needed to deploy a staple 100 from the plunger 322.

The link 308 provides articulation between the handle trigger 306 and plunger 322 allowing the transfer of the force on the handle trigger 306 to deploy the staple 100. The cam 310 allows for the control of the plunger 322, rod 324 and track 326 complex to appropriately actuate the swivel channel 320 and return the system back to its starting position.

The upper head housing 312 provides shape to the head of the device, helps secure the main channel 318 and swivel channel 320, and channels the plunger 322. The inner lower head housing 314 provides for attachment of the main channel 318, swivel channel 320 and track 326. The outer lower head housing 316 provides shape to the head of the device, creates space between the inner 314 and outer 316 housing for the array of staples, and channels the plunger 322.

The main channel 318 is a chute into which the staples 100 advance, one at a time, and directs the path of the staple 100 as it is deployed by the plunger 322 through tissue. The swivel channel 320 is a chute that swivels into position through tissue to receive the staple 100 that is advancing from the main channel 318. The swivel channel 320 is actuated by the plunger 322, rod 324, track 326 mechanism.

The plunger 322 is a device that transmits the force of the handle trigger 306 being squeezed to the advancement and locking of the staple 100. The rod 324 actuates the swivel channel 320 to swing into position. The track 326 controls the advancement of the plunger 322 and rod 324 to actuate the swivel channel 320.

The power for advancing, forming and ejecting the staple 100 is provided by the manipulative force of the surgeon. This force is transmitted to the plunger 322 by means of a handle trigger 306 that is linked inside the housing. By pulling the handle trigger 306 towards the fixed position of the handle housing 302 and 304, the plunger 322 is pushed forward to carryout the advancement and locking of the staple 100. After the staple 100 has been deployed, a spring that relates to the plunger 322 returns the plunger 322 and with it the handle trigger 306 to their initial position, and prepared for repeating the cycle with the next staple.

In its function as a device to suture tissue, the fixed arm on the end of the main channel 318 is pushed through one side of the tissue to be closed. The other side of the tissue is pulled over to meet the tissue the fixed arm has penetrated. The handle trigger 306 is closed by manipulative force of the surgeon. The handle trigger's activation causes the advancement of the link 308, which provides articulation between the handle trigger 306 and the plunger 322. This advances the plunger 322, which causes two coordinated events.

One, the plunger 322 causes the rod 324 to advance and swing the swivel channel 320 into the closed position. This effect causes the swivel channel 320 to penetrate the second side of the tissue and approximates the end of the swivel channel 320 to the end of the main channel 318. This creates a complete channel through the tissue for the staple 100 to travel through.

Two, the other effect of the plunger 322 is to advance the staple 100, which has been moved into the main channel 318. The plunger 322 forces the staple 100 through the channels until the arrowhead or connector head of the staple returns to meet the retainer, penetrates, and locks in place.

After this the trigger handle 306 is released and the device is pulled away from the tissue leaving the staple 100 secured in place. The delivery system resets to prepare for the application of the next staple. This is facilitated by the use of tension devices within the device such as springs and the use of a cam 310 to reset the position of the rod mechanism. Soft tissue tensioning is controlled by how much tissue is placed within the device.

This device is markedly distinguishable over other deliver systems for absorbable staples. Other systems rely on pushing a staple through the tissue to lock. The present system employs the use of channels that penetrate the tissue and then provide a tunnel for the advancement of the staple. Most one-piece staples that are delivered with the use of semi-automatic devices such as metal staples must be bent over an anvil. The present device advances and locks the staple by use of the axial force transferred to it by the plunger. This force advances the staple and locks the staple arrowhead or connector head into the retainer.

EXAMPLE 1

A one-piece bioabsorbable staple for tissue closure, especially for fascia closure, is made from polydiaxanone. The staple is fashioned to a pliable suture material with a diameter of, for example, #0, #1, or #2 and a length of, for example, 3 cm or 4 cm. The finished staple is double ended with a retainer at one end and an arrow head at the other end.

Figure 17:
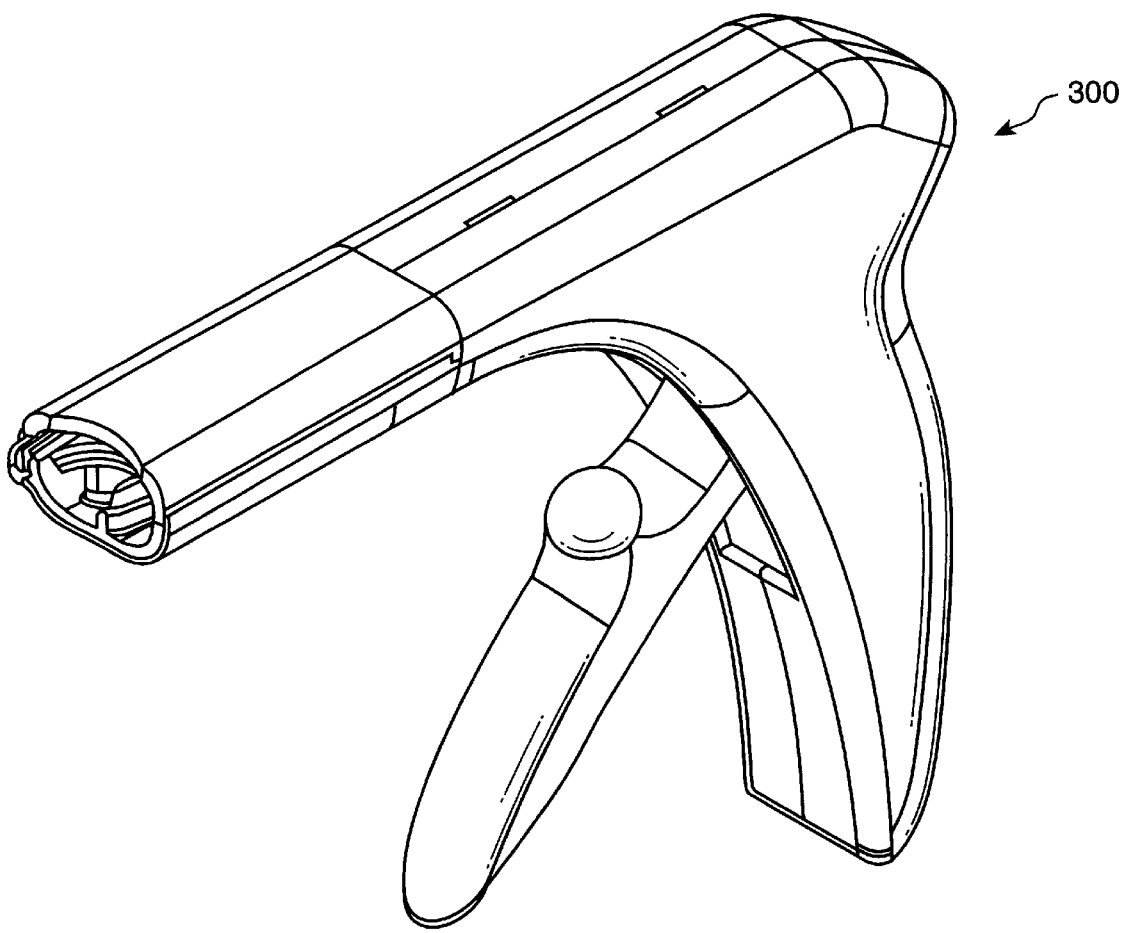
FIG. 17 shows a semi-automatic device for applying one or more bioabsorbable staples.
Figure 18:
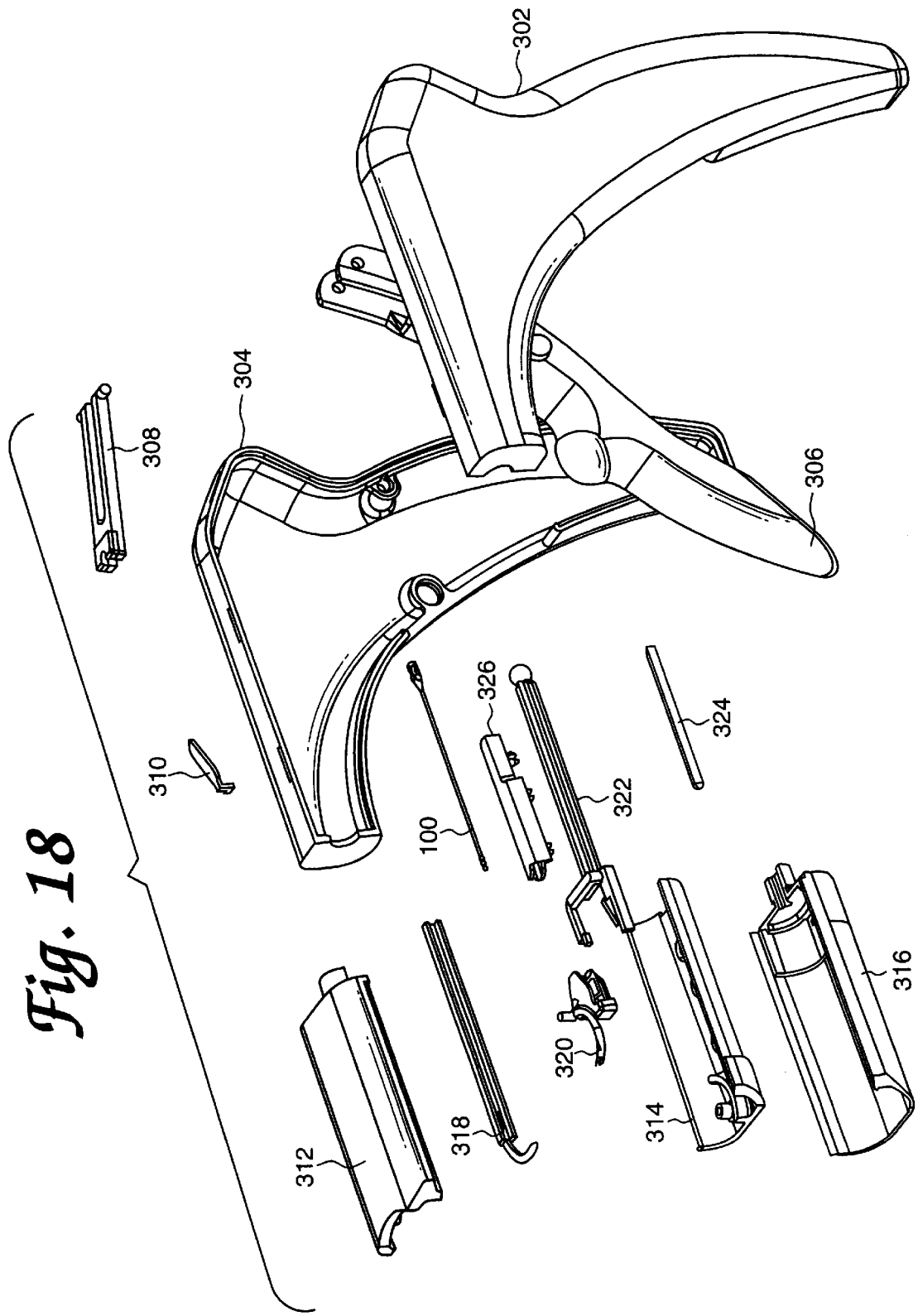
FIG. 18 is an exploded view of the semi-automatic device of FIG. 17.
Figure 19:
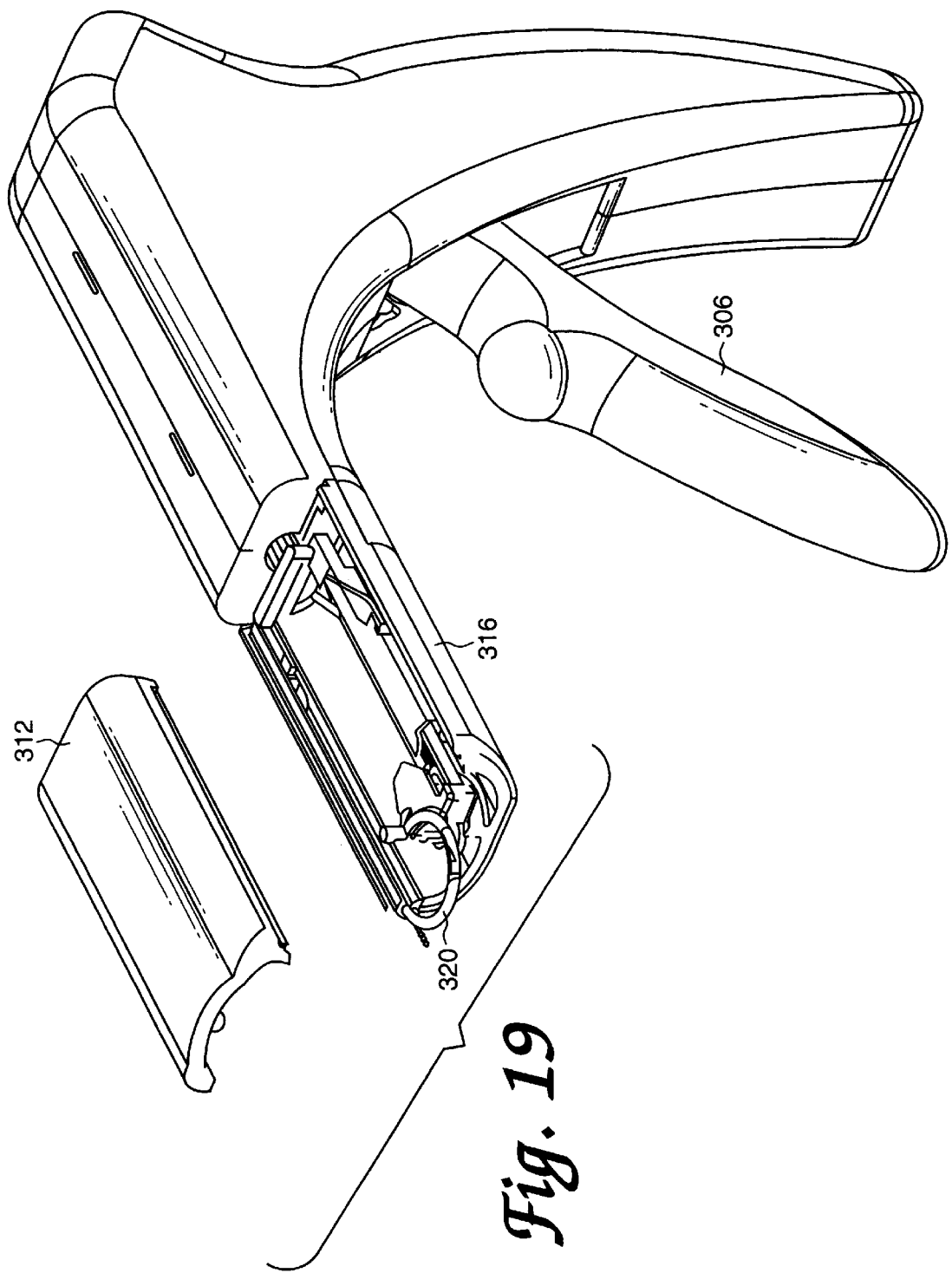
FIG. 19 is a view of the semi-automatic device of FIG. 17 with the upper head housing 312 removed.
Figure 20:
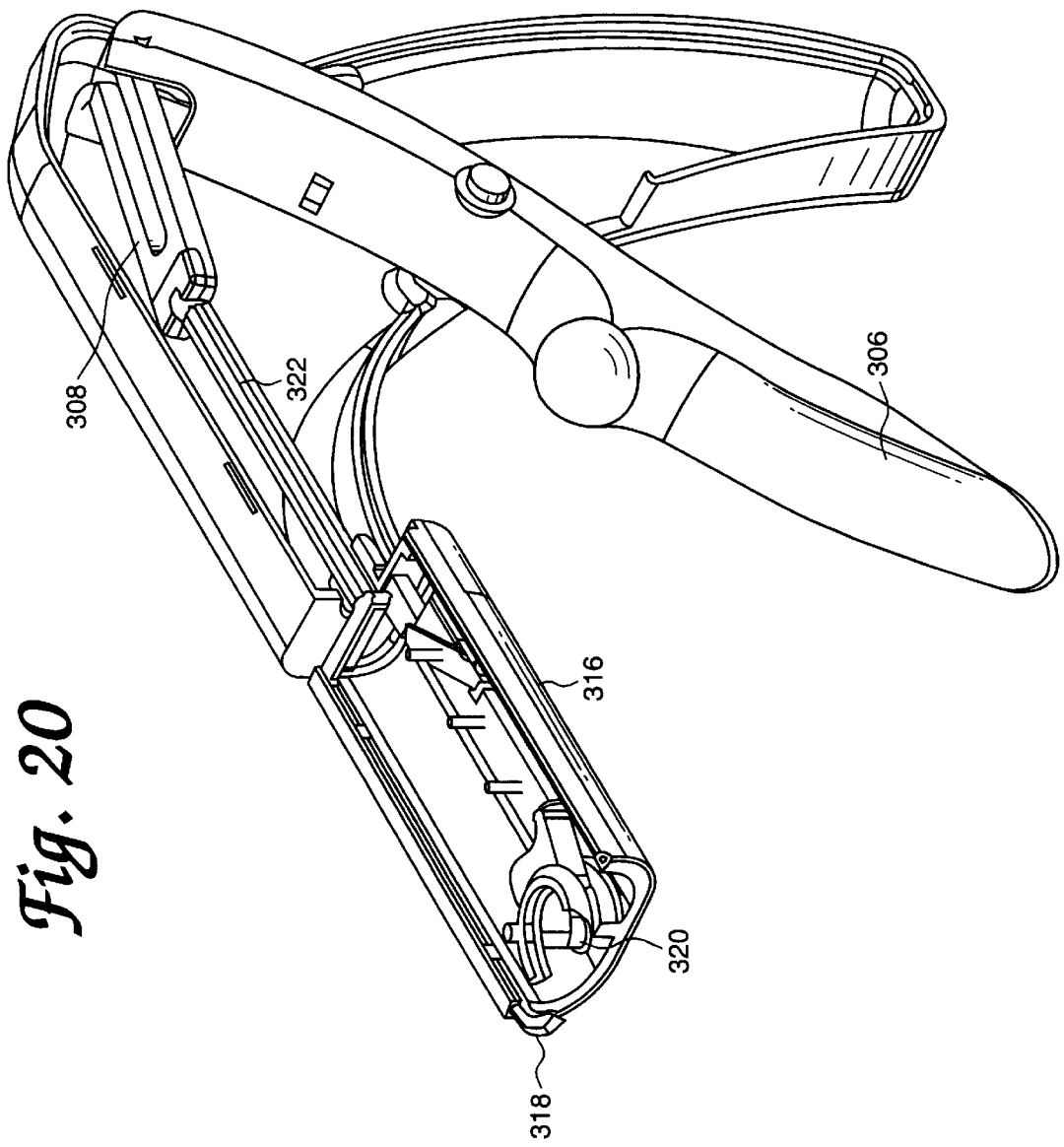
FIG. 20 is a view of the semi-automatic device of FIG. 17 with the upper head housing 312 and the right handle housing 302 removed.
Figure 21:
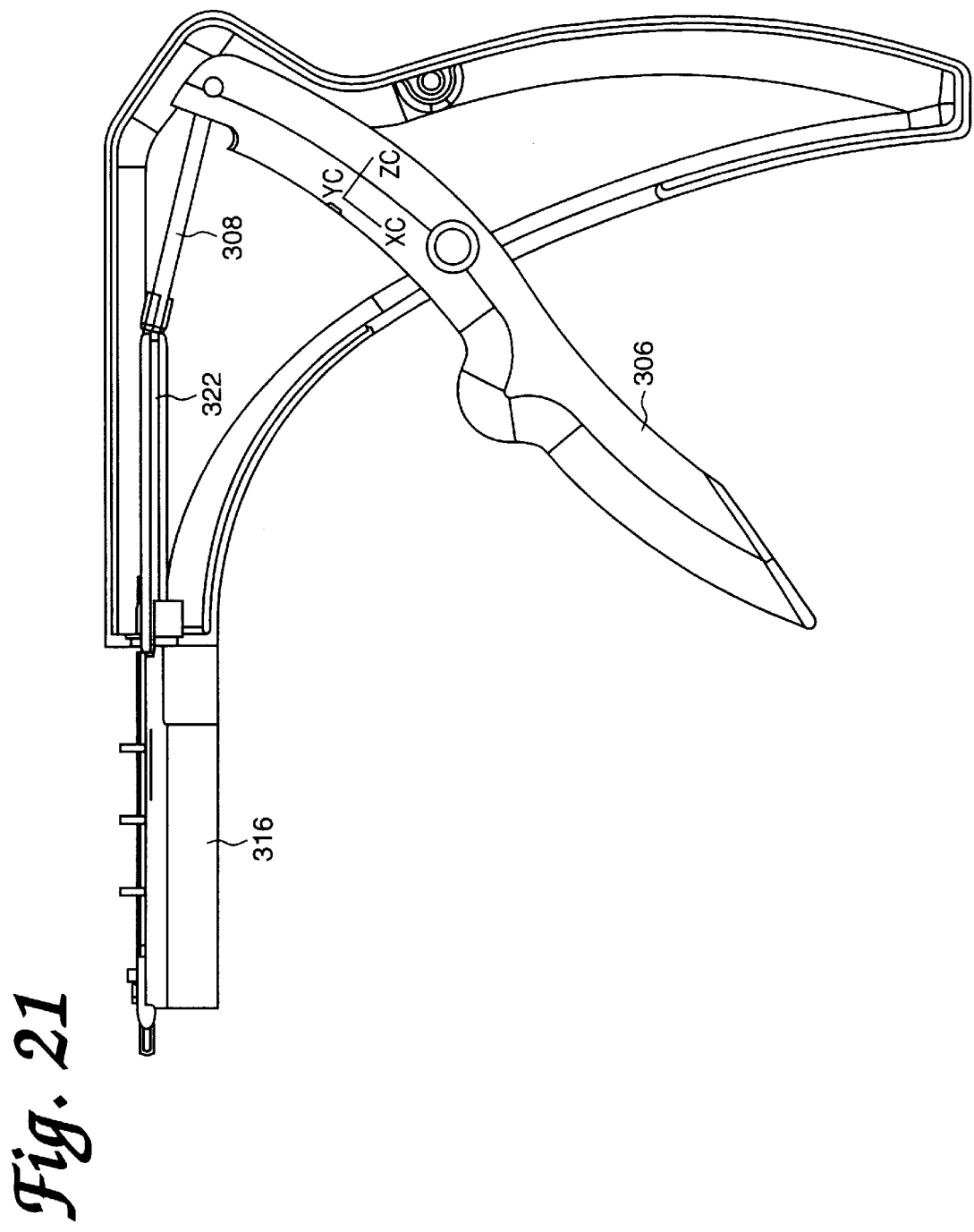
FIG. 21 is a side view of the semi-automatic shown in FIG. 20.

The staple is sterilized and used with a sterile self-contained delivery system, as shown in FIG. 17. The staples are packed in packages of 10 to 50 staples per unit. The delivery system instrument is used to grasp and hold the tissue, e.g., fascia. The instrument is spring loaded and the delivery end of the instrument and handle resemble a pistol with a swivel barrel option. The staple is then forced through the tissue and locked into the retainer. Soft tissue tensioning is controlled by how much soft tissue is placed within the device. The inserted staple has an ellipsoid structure.

Thus, in this Example, the method comprises the steps of grasping and holding the tissue to be closed, forcing the one-piece bioabsorbable staple through the tissue, and locking the staple.

EXAMPLE 2

A two-piece bioabsorbable staple for tissue closure is made from copolymerized glycolic acid and lactic acid (polysorb). The piece of the staple is fashioned with a pliable suture material having a diameter of, for example, 0.5 to 0.6 mm, a staple width of 4.5 to 7 mm, and a staple leg length of, for example, 3 to 4 mm. The finished staple is made of an elongate body having a leg connected to an arrow head at each end and a second elongate body having a retainer with an eyelet at each end.

The staple is sterilized and used with a sterile self-contained delivery system, as shown in FIG. 17. The staples are packed in packages of 10 to 50 staples per unit. The delivery system instrument is used to grasp and hold the tissue, e.g., fascia. The instrument is spring loaded and the delivery end of the instrument and handle resemble a pistol with a swivel barrel option. The staple is then forced through the tissue and locked into the retainer. Soft tissue tensioning is controlled by how much soft tissue is placed within the device. The inserted staple has an ellipsoid or curvilinear structure with convexity out for maximum purchase of soft tissue.

Thus, in this Example, the method comprises the steps of grasping and holding the tissue to be closed, forcing the two-piece bioabsorbable staple through the tissue, and locking the staple.

EXAMPLE 3

A one-piece bioabsorbable staple for tissue closure, especially for fascia closure, is made from polydiaxanone. The staple is fashioned to a pliable suture material with a diameter of, for example, #0, #1, or #2 and a length of, for example, 3 cm or 4 cm. The finished staple is double ended with a retainer at one end and a connector head at the other end, as shown in FIGS. 8–16.

The staple is sterilized and used with a sterile self-contained delivery system, as shown in FIG. 17. The staples are packed in packages of 10 to 50 staples per unit. The delivery system instrument is used to grasp and hold the tissue, e.g., fascia. The instrument is spring loaded and the delivery end of the instrument and handle resemble a pistol with a swivel barrel option. The staple is then forced through the tissue and locked into the retainer. Soft tissue tensioning is controlled by how much soft tissue is placed within the device. The inserted staple has an ellipsoid structure.

Thus, in this Example, the method comprises the steps of grasping and holding the tissue to be closed, forcing the one-piece bioabsorbable staple through the tissue, and locking the staple.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. A device for applying one or more staples to tissue, comprising:

a) a main body portion having a nose portion connected to a handle portion, wherein the nose portion comprises:
   i) a main channel,
   ii) a swivel channel,
   iii) a rod in contact with the swivel channel, and
   iv) a plunger in contact with the main channel and the rod, and wherein the handle portion comprises a link in contact with the plunger; and b) a handle trigger reciprocately connected to the link of the handle portion of the main body portion, wherein activation of the handle trigger causes advancement of the link which advances the plunger which causes
   i) the rod to advance and swing the swivel channel into contact with the main channel and
   ii) advancement of a staple through the main channel and the swivel channel.

2. The device of claim 1, wherein the device is semi-automatic.

3. The device of claim 1, further comprising a cam and spring in contact with the plunger.

4. The device of claim 1, further comprising an inner lower head housing for attachment of the main channel and the swivel channel.

5. The device of claim 4, further comprising an upper head housing in contact with an outer lower head housing, wherein the upper head housing and the outer lower head housing surround the nose portion of the main body portion.

6. A method for closure of a tissue, comprising the steps of:

a) grasping and holding a tissue to be closed;
   b) forcing a bioabsorbable staple through the tissue with the device of claim 1; and
   c) locking the staple.

7. The method of claim 6, wherein said forcing step further comprises:

i) pushing an end of the main channel through a first side of the tissue to be closed,
   ii) pulling a second side of the tissue into contact with the first side of the tissue,
   iii) pushing an end of the swivel channel through the second side of the tissue and into contact with the end of the main channel, and
   iv) advancing a staple through the main channel and the swivel channel.

* * * * *